US006972181B2

(12) United States Patent
Burstein

(10) Patent No.: US 6,972,181 B2
(45) Date of Patent: Dec. 6, 2005

(54) DIFFERENTIAL DIAGNOSIS OF CANCER AND OTHER CONDITIONS BASED ON EXPRESSION OF P63

(75) Inventor: David E. Burstein, New York, NY (US)

(73) Assignee: Mount Sinai School of Medicine of New York University, New York, NY (US)

( * ) Notice: Subject to any disclaimer, the term of this patent is extended or adjusted under 35 U.S.C. 154(b) by 504 days.

(21) Appl. No.: 10/043,502

(22) Filed: Jan. 9, 2002

(65) Prior Publication Data

US 2002/0094547 A1   Jul. 18, 2002

Related U.S. Application Data

(60) Provisional application No. 60/261,603, filed on Jan. 12, 2001.

(51) Int. Cl.[7] .............................................. G01N 33/53

(52) U.S. Cl. .......................... 435/7.23; 435/6; 436/64; 436/501; 436/518

(58) Field of Search ............................... 435/7.1, 7.23, 435/6; 436/501, 503, 65, 518

(56) References Cited

OTHER PUBLICATIONS

HiBi et al., (2000, Proc. Natl. Acad. Sci. USA., vol. 97, pp. 5462-5467).*
Syllabus with the title "Pathology of Lung Cancer" downloaded on Dec. 9, 2004 from url>>http://www.metrohelath.org/clinical/pathology/syllabus/carcinoma.asp, pp. 1-11.*
OMIM with #603273 (note p. 1, first paragraph) downloaded on Dec. 10, 2004 from url>>www.ncbi.nlm.nih.go.*
Wu et al., (2003, Cancer Research, vol. 63, pp. 2351-2357).*
Wang et al., (2002, Hum. Pathol. vol. 33, pp. 921-926).*
Hall et al., Carcinogenesis 2000; 21: 53-60.
Parsa et al., J. Invest. Dermatol. 1999; 113:1099-1105.
Yamaguchi et al., Int. J. Cancer 2000; 86:684-89.
Levrero et al., J. Cell Science 2000; 113:1661-70.

* cited by examiner

*Primary Examiner*—Misook Yu
(74) *Attorney, Agent, or Firm*—Darby & Darby

(57) ABSTRACT

This invention relates to methods of distinguishing among various types of differentiated and undifferentiated epithelial carcinomas, and non-epithelial carcinomas, by detecting the presence of p63 nucleic acid or protein expression. The invention also provides methods for detecting p63 nucleic acids and proteins, as well as methods for diagnosing and treating certain tumors based on whether the tumors express p63.

7 Claims, No Drawings

DIFFERENTIAL DIAGNOSIS OF CANCER AND OTHER CONDITIONS BASED ON EXPRESSION OF P63

This application claims priority from provisional patent application No. 60/261,603, filed Jan. 12, 2001.

The research leading to the present invention was supported, in part, by the National Cancer Institute Grant No. R21-CA81362. Accordingly, the U.S. Government may have certain rights in the invention.

FIELD OF THE INVENTION

The present invention relates to a gene product, referred to herein as p63, and to nucleic acids, including the gene, mRNAs, and cDNAs, encoding it, in particular, to methods of using the gene and gene product to diagnose and/or treat certain diseases and disorders such as cancer. The invention also relates to kits which may be used in such diagnostic and treatment methods.

BACKGROUND OF THE INVENTION

The nuclear protein p63, located on chromosome 3q, has been shown to possess homology with p53, a tumor-suppressor gene encoding a multi-functional DNA-binding protein important in cell cycle and cell death regulation. p63 exists in three isoforms, each of which can encode two categories of transcripts under the control of two alternative promoters. The first encodes full length proteins with an N-terminal transactivation domain that, like p53, can activate transcription and induce apoptosis. The second encodes truncated proteins lacking the N-terminal transactivation domain ($\Delta$Np63), and potentially acting in a dominant-negative manner to suppress transactivation by p53 and/or full length p63.

Little is known about the function of p63. Evidence suggests that p63 is necessary for normal development (Levrero et al., J. Cell Sci. 2000, 113:1661–70). Immunohistochemical studies using an anti-p63 polyclonal antiserum show that the protein is widely detectable, with predominant association in the proliferative compartments in epithelia but also in non-proliferative populations (Hall et al., Carcinogenesis 2000, 21:153–60). Normal human epidermis, hair follicles, and stratified epidermal cultures show p63 expression primarily in cells with proliferative potential, particularly basal cells, and not in cells undergoing terminal differentiation (Parsa et al., J. Invest. Dermatol. 1999, 113: 1099–1105). The p63 RNA present in the basal cells was mainly truncated, potentially dominant-negative isotypes (Parsa et al., supra).

Investigators have studied p63 expression in neoplasms. In keratinocyte squamous cell carcinomas, the number of cells containing p63 and their distribution depends on the degree of anaplasia (Parsa et al., supra). However, p63 does not yet have a defined role in neoplasia and other physiological and pathological situations (Hall et al., supra). Thus, there is a need in the art to determine what, if any role p63 plays in neoplasms and cancer.

SUMMARY OF THE INVENTION

The present invention are methods for detecting p63 nucleic acid and protein expression in a cell or tissue that can be used for diagnostic and prognostic purposes. Such methods include nucleic acid hybridization, PCR and RT-PCR, and various protein assays employing antibodies that bind to p63 polypeptides. In a preferred embodiment, the protein assay immunohistochemical staining using the anti-p63 4A4 monoclonal antibody (Santa Cruz Biotechnology, Inc., Santa Cruz, Calif.). The present invention also provides a kit comprising the reagents required for detection of p63 nucleic acids or polypeptides.

The present invention also provides methods for distinguishing differentiated lung cancers from undifferentiated lung cancers by evaluating lung tissue for the expression of p63 nucleic acids or proteins. In particular, the expression of p63 indicates that the lung cancer is a differentiated carcinoma and absence of p63 expression is indicative of a undifferentiated carcinoma.

In a preferred embodiment, the undifferentiated lung cancer is a small cell undifferentiated carcinoma and the differentiated lung cancer is a poorly differentiated squamous cell carcinoma, a moderately differentiated squamous cell carcinoma, a well-differentiated squamous cell carcinoma, an adenosquamous carcinoma or an adenocarcinoma.

The present invention also provides methods of distinguishing an epithelial squamous cell carcinoma from a carcinoma without squamous differentiation or squamous differentiation potential or a non-epithelial cell tumor by detecting p63 nucleic acid or protein expression in cells derived from a carcinoma. In particular, p63 expression indicates that the carcinoma is an epithelial squamous cell carcinoma and the absence of p63 expression indicates that the carcinoma is a carcinoma without squamous differentiation potential or a non-epithelial cell tumor.

In a preferred embodiment, the p63 positive cells are squamous epithelial cells, transitional cells or glandular epithelial cells and the p63 negative cells are glandular carcinoma cells, or most preferably, renal carcinoma cells.

Also provided by the present invention is a method for distinguishing a thyroid papillary carcinoma from another thyroid disorder in thyroid cells derived from a neoplasm, nodule, or enlargement by detecting p63 nucleic acid or protein expression. p63 expression is indicative of a papillary carcinoma and absence of p63 expression is indicative of a follicular adenomata, a medullary carcinoma, an anaplastic carcinoma or a Hurthle cell carcinoma.

The present invention also provides a method of distinguishing Hashimoto's thyroiditis from another inflammatory thyroid condition by detecting p63 nucleic acid or protein expression in inflammatory thyroid cell. The presence p63 nucleic acid or protein expression indicates that the pathology is Hashimoto's thyroiditis and the absence of p63 expression indicates that the inflammatory pathology is Grave's disease.

The present invention additionally provides a method for treating lung cancer in a patient by diagnosing the lung cancer as a squamous cell carcinoma by detecting p63 expression, followed by surgical resection of the p63-expressing tumor.

DETAILED DESCRIPTION OF THE INVENTION

The present invention provides a method for differentially distinguishing various types of cancer and other pathological conditions. For example, the invention permits distinguishing a specific type of lung cancer, such as a poorly differentiated squamous cell carcinoma, a moderately differentiated squamous carcinoma, a well differentiated squamous cell carcinoma, an adenosquamous carcinoma, and an adenocarcinoma, from an undifferentiated lung cancer, such as a small cell undifferentiated carcinoma (oat cell carcinoma). Alternatively, the invention provides for distinguishing papillary thyroid carcinoma from other thyroid neoplasms. In yet another embodiment, the invention provides for distinguishing transitional cell carcinomas (from the kidney and ureter) from renal cell carcinomas. P63 detection may be employed in any differential diagnosis between a tumor of squamous origin, differentiation or squamous potential, and a tumor without squamous origin, differentiation or potential.

In another aspect, the invention permits detection or diagnosis of precancerous dysplasia, intra-epithelial neoplasms, or cancer (malignancy) in epithelial cells by detecting p63 expression in surface (not basal stem) epithelial cells, which ordinarily lack p63 expression. For example, cervical cells obtained by non-traumatic brushing or lavage that express p63 are likely in a state of pre-malignancy or have become malignant. Other cell types amenable to this diagnostic approach include, but are not limited to, squamous epithelia (e.g., mouth, esophagus, trachea, anus); transitional cells (e.g., bladder, ureter, urethra, epithelia lining the respiratory tract); glandular epithelial cells (e.g., thyroid, endometrium, endocervix); and other cells that are or have the capacity to become squamous. This aspect of the invention yields better results when the basal stem cells, that continuously divide to reform the epithelial tissue, are not assayed, since these cells express p63 endogenously.

In each case, the method comprises detecting p63 expression in cells from the cancer or other condition. The invention is based, in part, on the observation that tumors or conditions arising from non-squamous epithelia having the capacity to undergo squamous differentiation are capable of expressing p63. In contrast, tumors that never undergo squamous differentiation do not express p63.

In the case of cancer, p63 expression indicates that the lung cancer is a differentiated lung cancer. The absence of p63 expression indicates that the lung cancer is likely an undifferentiated lung cancer. The invention specifically provides for distinguishing poorly differentiated squamous carcinoma (p63 expression) from small cell undifferentiated carcinoma (no p63 expression). In another embodiment, the invention provides for distinguishing bronchioloalveolar carcinoma (no p63 expression) from adenocarcinoma with alveolar spread pattern (p63 expression). The invention further provides for diagnosing a new subtype of adenosquamous carcinoma marked by basal p63 staining.

In the case of distinguishing between transitional cell and renal cell cancer, p63 expression indicates that the renal cancer is a transitional cell carcinoma, and the absence of p63 expression indicates that the renal cancer is a renal cell carcinoma. For example, the invention provides for distinguishing upper uretal or renal pelvic transitional carcinoma (urothelial carcinoma), in which cells express p63, from renal cell carcinoma or adrenal carcinoma, in which the cells are negative for p63 expression.

In the case of thyroid cancer, p63 expression indicates that the thyroid cancer is a papillary thyroid carcinoma, and the absence of p63 expression indicates that the thyroid cancer is a different thyroid neoplasm. In particular, the invention provides for distinguishing papillary carcinoma, in which cells are positive for p63 expression, from follicular carcinoma, medullary carcinoma, follicular adenoma, Hurthle cell adenoma, Hurthle cell carcinoma, and nodular goiter in which cells are negative for p63 expression.

In addition, the invention advantageously provides for differentiation of noncancerous thyroid conditions. In particular, it provides for diagnosing antibody-positive and antibody-negative Hashimoto's thyroiditis. This is particularly advantageous in the case of antibody-negative Hashimoto's. It further permits distinguishing Hashimoto's thyroiditis (p63 positive) from other inflammatory thyroid conditions, such as Grave's disease (which is p63 negative).

Various methods are available to detect p63 expression, including biochemical assays, immunoassays, Northern and reverse-transcriptase polymerase chain reaction (RTPCR) assays, and the like. In a specific embodiment, detecting p63 expression comprises detecting expression of p63 protein. More particularly, detecting p63 protein expression comprises detecting the p63 protein with an immunoassay. In specific embodiments exemplified infra, the immunoassay is an immunohistochemical assay or an immunocytopathology assay.

The assays of the invention can be performed on various cell samples. For example, tumor cell tissue obtained by biopsy, resection, or other technique can be tested. Alternatively, cytological samples can be tested.

The invention further provides a method of treatment of lung cancer in a patient. The method comprises administering a chemotherapeutic agent to a patient diagnosed with a small cell undifferentiated carcinoma lung cancer, wherein the small cell undifferentiated carcinoma is distinguished from a squamous cell carcinoma by detecting an absence of p63 expression in cells from the lung cancer. In another embodiment, the method comprises surgically resecting a squamous cell carcinoma from a lung of a patient diagnosed with squamous cell carcinoma lung cancer, wherein the squamous cell carcinoma is distinguished from a small cell carcinoma by detecting p63 expression in cells from the lung cancer.

As used herein, the term "p63" refers to a protein homologous to the tumor suppressor protein p53, which contains a multi-functional DNA-binding protein important in cell cycle and cell death regulation. p63 exists in three isoforms, each of which can encode two categories of transcripts under the control of two alternative promoters. The first encodes full length proteins with an acidic N-terminal transactivation domain that, like p53, can activate transcription and induce apoptosis. The second encodes truncated proteins lacking the N-terminal transactivation domain ($\Delta$Np63), and potentially acting in a dominant-negative manner to suppress transactivation by p53 and full length p63. Unless otherwise specified, p63 means any of the three isoforms. The three p63 splice forms, $\alpha$, $\beta$, and $\gamma$ may be differentially expressed in tumors.

A tumor is "p63 positive" or has detectable p63 expression when any cells in the tumor express p63. A tumor is "p63 negative" or has no detectable p63 expression when no cells express p63 at detectable levels.

As used herein, the term "cancer" refers to any malignant tumor, particularly arising in the lung, kidney, or thyroid. The cancer manifests itself as a "tumor" or tissue comprising malignant cells of the cancer. Examples of tumors that can be detected, diagnosed and treated according to the invention include sarcomas and carcinomas such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma. As noted above, the invention specifically permits differential diagnosis of lung, kidney, and thyroid tumors.

In particular, the invention permits differential diagnosis of various lung cancers. These include poorly differentiated, moderately differentiated, and high differentiated squamous cell carcinomas; bronchioloalveolar carcinoma, carcinoid, and small cell undifferentiated carcinoma. Bronchioloalveolar carcinoma is a well-differentiated adenocarcinoma probably derived from lung alveolar epithelium. Carcinoid is a generally much less aggressive form of tumor than small cell undifferentiated. Small cell undifferentiated carcinoma is a highly aggressive cancer.

The present invention also advantageously provides for assessing the tumorigenic potential of thyroid nodules. At present, detection of thyroid nodules leads to fine needle aspiration to obtain cells from the nodule. Cytologic analysis of these cells can provide an indication of whether or not they are neoplastic or malignant. For example, follicular adenomas and papillary carcinoma may present as thyroid nodules. Fine needle aspiration can fail to yield cells amenable to definitive pathological analysis. Detecting p63 expression in nodule cells deemed neoplastic permits a confident diagnosis of papillary carcinoma; the absence of p63 expression leads to a diagnosis of a different pathology, such as follicular adenoma.

Accuracy in the pre-surgical determination of malignancy in thyroid nodules is essential, in order to avoid unnecessary surgery for non-malignant thyroid conditions presenting as a nodule or enlargement. Although pre-surgical testing including ultrasonographic scans and fine needle aspiration cytologic evaluation is useful for definitively identifying some of these lesions pre-surgically, in many cases, the definitive decision to perform surgery or to choose the appropriate surgery cannot be made.

For example, papillary thyroid carcinoma may have cytologic features on fine needle aspiration which are considered abnormal or suspicious, but non-definitive, or may have features which are indistinguishable from benign entities such as follicular adenomas. In these and other circumstances, detection and evaluation of p63 at the gene, mRNA, or protein level will allow for definitive diagnosis, reducing either unnecessary surgery for benign entities, inappropriate delays of months to years for surgical removal of malignancy, and reduce the need for second surgical procedures, such as when a papillary carcinoma is misdiagnosed as a benign adenoma. p63 may be detected alone, or in a multiplex panel with non-p63 probes, e.g., other antibodies, on a DNA or proteomics chip.

As used herein, the term "isolated" means that the referenced material is removed from the environment in which it is normally found. Thus, an isolated biological material can be free of cellular components, i.e., components of the cells in which the material is found or produced. In the case of nucleic acid molecules, an isolated nucleic acid includes a PCR product, an isolated mRNA, a cDNA, or a restriction fragment. In another embodiment, an isolated nucleic acid is preferably excised from the chromosome in which it may be found, and more preferably is no longer joined to non-regulatory, non-coding regions, or to other genes, located upstream or downstream of the gene contained by the isolated nucleic acid molecule when found in the chromosome. In yet another embodiment, the isolated nucleic acid lacks one or more introns. Isolated nucleic acid molecules include sequences inserted into plasmids, cosmids, artificial chromosomes, and the like. Thus, in a specific embodiment, a recombinant nucleic acid is an isolated nucleic acid. An isolated protein may be associated with other proteins or nucleic acids, or both, with which it associates in the cell, or with cellular membranes if it is a membrane-associated protein. An isolated organelle, cell, or tissue is removed from the anatomical site in which it is found in an organism. An isolated material may be, but need not be, purified.

The term "purified" as used herein refers to material that has been isolated under conditions that reduce or eliminate the presence of unrelated materials, i.e., contaminants, including native materials from which the material is obtained. For example, a purified protein is preferably substantially free of other proteins or nucleic acids with which it is associated in a cell; a purified nucleic acid molecule is preferably substantially free of proteins or other unrelated nucleic acid molecules with which it can be found within a cell. As used herein, the term "substantially free" is used operationally, in the context of analytical testing of the material. Preferably, purified material substantially free of contaminants is at least 50% pure; more preferably, at least 90% pure, and more preferably still at least 99% pure. Purity can be evaluated by chromatography, gel electrophoresis, immunoassay, composition analysis, biological assay, and other methods known in the art.

Methods for purification are well-known in the art. For example, nucleic acids can be purified by precipitation, chromatography (including preparative solid phase chromatography, oligonucleotide hybridization, and triple helix chromatography), ultracentrifugation, and other means. Polypeptides and proteins can be purified by various methods including, without limitation, preparative disc-gel electrophoresis, isoelectric focusing, HPLC, reversed-phase HPLC, gel filtration, ion exchange and partition chromatography, precipitation and salting-out chromatography, extraction, and countercurrent distribution. For some purposes, it is preferable to produce the polypeptide in a recombinant system in which the protein contains an additional sequence tag that facilitates purification, such as, but not limited to, a polyhistidine sequence, or a sequence that specifically binds to an antibody, such as FLAG and GST. The polypeptide can then be purified from a crude lysate of the host cell by chromatography on an appropriate solid-phase matrix. Alternatively, antibodies produced against the protein or against peptides derived therefrom can be used as purification reagents. Cells can be purified by various techniques, including centrifugation, matrix separation (e.g., nylon wool separation), panning and other immunoselection techniques, depletion (e.g., complement depletion of contaminating cells), and cell sorting (e.g., fluorescence activated cell sorting [FACS]). Other purification methods are possible. A purified material may contain less than about 50%, preferably less than about 75%, and most preferably less than about 90%, of the cellular components with which it was originally associated. The "substantially pure" indicates the highest degree of purity which can be achieved using conventional purification techniques known in the art.

A "sample" as used herein refers to a biological material which can be tested, e.g., for the presence of p63 polypeptides or p63 nucleic acids, e.g., to identify cells that specifically express the p63 gene and its gene product. Such samples can be obtained from any source, including tissue biopsies, blood and blood cells, pleural effusions, pericardial effussions, cerebrospinal fluid (CSF), urine, ascites fluid, cyst fluids, bronchial aspiration, bronchoscopic washes and lavages, peritoneal washes, brushes and brush specimens, fine needle aspiration, pap smear, and cell culture. In preferred embodiments samples are obtained, e.g., in a biopsy, from cancerous tissue (e.g., a tumor) or from tissue that is suspected of being cancerous or of containing cancer cells. In one particularly preferred embodiment samples are obtained from lung tissue. In another preferred embodiment for testing epithelial cells for dysplasia, intra-epithelial pre-malignant changes, or malignancy, the cells are obtained from the surface by gentle brushing, washing, or lavage to avoid obtaining p63-positive basal cells.

Non-human animals include, without limitation, laboratory animals such as mice, rats, rabbits, hamsters, guinea pigs, etc.; domestic animals such as dogs and cats; and, farm animals such as sheep, goats, pigs, horses, and cows.

In preferred embodiments, the terms "about" and "approximately" shall generally mean an acceptable degree of error for the quantity measured given the nature or precision of the measurements. Typical, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

The invention provides for administration of a therapeutically effective treatment in conjunction with the diagnostic and prognostic methods. The term "therapeutically effective" refers to that amount of a treatment regimen that is sufficient to result in a desired activity. Thus, as used to describe a cancer therapy, a therapeutically effective treatment refers to the amount of a chemotherapeutic compound or compositions, radiation, resection, or gene therapy, for example, that is sufficient to produce an effective outcome, such as tumor regression, increase time of survival, increased time of remission, and the like.

The phrase "pharmaceutically acceptable" refers to molecular entities and compositions that are physiologically tolerable and do not typically produce an allergic or similar untoward reaction (for example, gastric upset, dizziness and the like) when administered to an individual. Preferably, and particularly where a vaccine is used in humans, the term "pharmaceutically acceptable" may mean approved by a regulatory agency (for example, the U.S. Food and Drug Agency) or listed in a generally recognized pharmacopeia for use in animals (for example, the U.S. Pharmacopeia).

The term "carrier" refers to a diluent, adjuvant, excipient, or vehicle with which a compound is administered. Sterile water or aqueous saline solutions and aqueous dextrose and glycerol solutions are preferably employed as carriers, particularly for injectable solutions. Exemplary suitable pharmaceutical carriers are described in "Remington's Pharmaceutical Sciences" by E. W. Martin.

Detection of p63 Expression

A variety of methods can be employed for diagnostic and prognostic methods using reagents. For example, using the methods described here it is possible to detect expression of a p63 nucleic acid or protein in cells or tissues from an individual, such as in cells or tissues in a sample (e.g., from a biopsy) obtained or derived from an individual subject or patient. As explained above, p63 nucleic acids and polypeptides are expressed at elevated levels in certain cancerous cells and tissues including, for example, in the various types of cancer and tumor cells and tissues identified above, and not expressed in other tumor types.

Thus, using the methods described here (as well as other methods known in the art) a skilled artisan may detect expression of p63 in a sample of cells or tissue from an individual, and may thereby detect and/or identify cells or tissue in that sample as being cancer cells or tissue of a particular pathological type. For example, in preferred embodiments a skilled artisan may use such methods to identify cells or tissue in a sample as being a particular type of cancer cell or tissue which is known to express elevated levels of a p63 nucleic acid or polypeptide. Such cancer cells and tissues may be, for example, any of the particular cancer and tumor cell/tissue types described supra. In certain preferred embodiments the particular type of cancer cell or tissue identified in such methods are lung cancer cells or tissue, such as cells or tissues of bronchogenic carcinoma, lung carcinoma or small cell lung carcinoma. By using such methods to detect cancer cells or tissue in an individual, a skilled user may thereby diagnose the presence of the cancer in that individual. Similarly, the absence of p63 expression provides information about the nature of the cancer.

In preferred embodiments the methods described herein are performed using pre-packaged diagnostic kits. Such kits may comprise at least one specific p63 nucleic acid or a p63 specific antibody reagent. The kit and any reagent(s) contained therein may be used, for example, in a clinical setting, to diagnose patients exhibiting or suspected of having a disorder such as a type of cancer.

A sample comprising a nucleated cell (of any cell type) from an individual may be used in such diagnostic and prognostic methods as a starting source for genomic nucleic acid and to detect mutations of a p63 gene. A sample comprising a cell of any cell type or tissue of any tissue type in which a p63 gene is expressed may also be used in such diagnostic methods, e.g., for detection of p63 gene expression or of p63 gene products (such as p63 proteins), as well as for identifying cells, particularly cancer and tumor cells, that express or do not express p63.

Immunoassays

The diagnostic and prognostic methods of the invention include ones that comprise detecting levels of a p63 protein or other p63 polypeptides and including functionally conserved variants and fragments thereof For example, antibodies directed against unimpaired, wild-type or mutant p63 gene products or against functionally conserved variants or peptide fragments of a p63 gene product may be used as diagnostic and prognostic reagents, e.g., to detect various types of cancer cells and tumors. Such reagents may be used, for example, to detect abnormalities in the level of p63 gene product synthesis or expression. Antibodies and immunoassay methods such as those described hereinbelow also have important in vitro applications for assessing the efficacy of treatments, e.g., for cancer. Compounds that may have beneficial effects on a disorder associated with abnormal p63 expression (e.g., any of the types of cancer identified supra) can be identified and a therapeutically effective dose for such compounds may be determined using such assays.

In vitro immunoassays can also be used to assess the efficacy of cell-based gene therapy for a cancer or other disorder associated with abnormal p63 expression. For example, antibodies directed against p63 polypeptides may be used in vitro to determine the level of p63 gene or polypeptide expression achieved in tumor cells. Such methods may be used to detect intracellular p63 gene products, preferably using whole cells, but also including cell lysates or extracts, to detect expression of p63 gene products.

The isolated cells may be cells derived from cell culture or from an individual (e.g., a biopsy sample from a patient suspected of having a type of cancer or other disorder associated with abnormal levels of p63 expression, or suspected of having a propensity for such a cancer or other disorder).

As one example, antibodies or fragments of antibodies may be used to detect the presence of a p63 gene product, a variant of a p63 gene product or fragments thereof, for example, by immunofluorescence techniques employing a fluorescently labeled antibody coupled with light microscopic, flow cytometric or fluorimetric detection methods.

In particularly preferred embodiments, antibodies or fragments thereof may also be employed histologically, for example in immunostaining, immunofluorescence or immunoelectron microscopy techniques, for in situ detection of a p63 gene product. In situ detection may be accomplished by removing a histological specimen (e.g., a tissue sample) from a patient and applying thereto a labeled antibody of the present invention or a fragment of such an antibody. The antibody or antibody fragment is preferably applied by overlaying the labeled antibody or antibody fragment onto a biological sample. Through the use of such a procedure, it is possible to detect, not only the presence of a p63 gene product, but also the gene product's distribution in the examined tissue. A wide variety of histological methods that are well known in the art (for example, staining procedures) can be readily modified by those skilled in the art without undue experimentation to achieve such in situ detection.

Immunoassays for p63 gene products will typically comprise incubating a biological sample (for example, a biological fluid, a tissue extract, freshly harvested cells or cell lysates) in the presence of a detectably labeled antibody that is capable of specifically binding a p63 gene product (including, for example, a functionally conserved variant or a peptide fragment thereof). The bound antibody may then be detected by any of a number of techniques well known in the art.

According to the invention, p63 polypeptide produced recombinantly or by chemical synthesis, and fragments or other derivatives or analogs thereof, including fusion proteins, may be used as an immunogen to generate antibodies that recognize the p63 polypeptide. Such antibodies include but are not limited to polyclonal, monoclonal, chimeric, single chain, Fab fragments, and an Fab expression library. The anti-p63 antibodies of the invention may be cross reactive, e.g., they may recognize p63 from different species. Polyclonal antibodies have greater likelihood of cross reactivity. Alternatively, an antibody of the invention may be specific for a single form of p63, such as murine p63. Preferably, such an antibody is specific for human p63. Antibodies for use in the invention can also be specific for a specific isoform of p63, such as any of the three p63 splice forms, α, β, and γ. Since p63 forms have different cellular functions, it will be useful to develop a panel consisting of an N-terminal-sequence specific antibody (that would detect only the full length p63 forms), and an antibody such as the one used in this study, that recognizes both full length and truncated Δ-N forms. Additional clinically useful differences in expression patterns are expected.

Various procedures known in the art may be used for the production of polyclonal antibodies to p63 polypeptides or derivatives or analogs thereof For the production of antibody, various host animals can be immunized by injection with the p63 polypeptide, or a derivative (e.g., fragment or fusion protein) thereof, including but not limited to rabbits, mice, rats, sheep, goats, etc. In one embodiment, the p63 polypeptide or fragment thereof can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (*bacille Calmette—Guerin*) and *Corynebacterium parvum*.

For preparation of monoclonal antibodies directed toward the p63 polypeptide, or fragment, analog, or derivative thereof, any technique that provides for the production of antibody molecules by continuous cell lines in culture may be used. These include but are not limited to the hybridoma technique originally developed by Kohler and Milstein (Nature 256:495–497, 1975), as well as the trioma technique, the human B-cell hybridoma technique (Kozbor et al., Immunology Today 4:72, 1983; Cote et al., Proc. Natl. Acad. Sci. U.S.A. 80:2026–2030, 1983), and the EBV-hybridoma technique to produce human monoclonal antibodies (Cole et al., in Monoclonal Antibodies and Cancer Therapy, Alan R. Liss, Inc., pp. 77–96, 1985). In an additional embodiment of the invention, monoclonal antibodies can be produced in germ-free animals (International Patent Publication No. WO 89/12690, published 28, Dec. 1989). In fact, according to the invention, techniques developed for the production of "chimeric antibodies" (Morrison et al., J. Bacteriol. 159:870, 1984; Neuberger et al., Nature 312:604–608, 1984; Takeda et al., Nature 314:452–454, 1985) by splicing the genes from a mouse antibody molecule specific for an p63 polypeptide together with genes from a human antibody molecule of appropriate biological activity can be used; such antibodies are within the scope of this invention. Such human or humanized chimeric antibodies are preferred for use in therapy of human diseases or disorders (described infra), since the human or humanized antibodies are much less likely than xenogenic antibodies to induce an immune response, in particular an allergic response, themselves.

According to the invention, techniques described for the production of single chain antibodies (U.S. Pat. Nos. 5,476,786 and 5,132,405 to Huston; U.S. Pat. No. 4,946,778) can be adapted to produce p63 polypeptide-specific single chain antibodies. Indeed, these genes can be delivered for expression in vivo. An additional embodiment of the invention utilizes the techniques described for the construction of Fab expression libraries (Huse et al., Science 246:1275–1281, 1989) to allow rapid and easy identification of monoclonal Fab fragments with the desired specificity for an p63 polypeptide, or its derivatives, or analogs.

Antibody fragments which contain the idiotype of the antibody molecule can be generated by known techniques. For example, such fragments include but are not limited to: the $F(ab')_2$ fragment which can be produced by pepsin digestion of the antibody molecule; the Fab fragments which can be generated by reducing the disulfide bridges of the $F(ab')_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of an p63 polypeptide, one may assay generated hybridomas for a product which binds to an p63 polypeptide fragment containing such epitope. For selection of an antibody specific to an p63 polypeptide from a particular species of animal, one can select on the basis of positive binding with p63 polypeptide expressed by or isolated from cells of that species of animal.

The foregoing antibodies can be used in methods known in the art relating to the localization and activity of the p63 polypeptide, e.g., for Western blotting, imaging p63 polypeptide in situ, measuring levels thereof in appropriate physiological samples, etc. using any of the detection techniques mentioned above or known in the art.

In a specific embodiment, antibodies that agonize or antagonize the activity of p63 polypeptide can be generated. Such antibodies can be tested using the assays described infra for identifying ligands.

Molecular Biological Assays

The diagnostic and prognostic methods of the invention include methods for assaying the level of p63 gene expression. A variety of methods known in the art may be used to detect assay levels of p63 nucleic acid sequences in a sample. For example, RNA from a cell type or tissue, such a tumor cell or tissue type, that is known or suspected to express the p63 gene may be isolated and tested utilizing hybridization or PCR techniques known in the art. The isolated cells may be, for example, cells derived from a cell culture or from an individual. The analysis of cells taken from a cell culture may be useful, e.g., to test the effect of compounds on the expression of a p63 gene, or alternatively, to verify that the cells are ones of a particular cell type that expresses a p63 gene.

As an example, and not by way of limitation, diagnostic methods for the detection of p63 nucleic acids can involve contacting and incubating nucleic acids (including recombinant DNA molecules, cloned genes or degenerate variants thereof) obtained from a sample with one or more labeled nucleic acid reagents, such as recombinant p63 DNA molecules, cloned genes or degenerate variants thereof, under conditions favorable for specifically annealing or hybridizing these reagents to their complementary sequences in the sample nucleic acids. Preferably the lengths of these nucleic acid reagents are at least 15 to 30 nucleotides. After incubation, all non-annealed or non-hybridized nucleic acids are removed. The presence of nucleic acids that have hybridized, if any such molecules exist, is then detected and the level of p63 nucleic acid sequences to which the nucleic acid reagents have annealed may be compared to the annealing pattern or level expected from a control sample (e.g., from a sample of normal, non-cancerous cells or tissues) to determine whether p63 nucleic acid is expressed at an elevated level.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ (melting temperature) of 55° C., can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6× SCC. High stringency hybridization conditions correspond to the highest $T_m$, e.g., 50% formamide, 5× or 6×SCC. SCC is a 0.15M NaCl, 0.015M Na-citrate. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50–9.51). For hybridization with shorter nucleic acids, i.e., oligonucleotides, the position of mismatches becomes more important, and the length of the oligonucleotide determines its specificity ( see Sambrook et al., supra, 11.7–11.8). A minimum length for a hybridizable nucleic acid is at least about 10 nucleotides; preferably at least about 15 nucleotides; and more preferably the length is at least about 20 nucleotides.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C. In a specific embodiment, "high stringency" refers to hybridization and/or washing conditions at 68° C. in 0.2×SSC, at 42° C. in 50% formamide, 4×SSC, or under conditions that afford levels of hybridization equivalent to those observed under either of these two conditions.

In a preferred embodiment of such a detection scheme, the nucleic acid from the cell type or tissue of interest may be immobilized, for example, to a solid support such as a membrane or a plastic surface (for example, on a nylon membrane, a microtiter plate or on polystyrene beads). After incubation, non-annealed, labeled p63 nucleic acid reagents may be easily removed and detection of the remaining, annealed, labeled p63 nucleic acid reagents may be accomplished using standard techniques that are well-known in the art.

Alternative diagnostic methods for the detection of p63 nucleic acids in patient samples or in other cell or tissue sources may involve their amplification, e.g., by PCR (see, for example, the experimental embodiment taught in U.S. Pat. No. 4,683,202) followed by detection of the amplified molecules using techniques that are well known to those of skilled in the art. The resulting level of amplified p63 nucleic acid may be compared to those levels that would be expected if the sample being amplified contained only normal levels of p63 nucleic acid, as normal cells or tissues, to determine whether elevated levels of a p63 nucleic acid are expressed.

In one preferred embodiment of such a detection scheme, a cDNA molecule is synthesized from an RNA molecule of interest (e.g., by reverse transcription). A sequence within the cDNA may then be used as a template for a nucleic acid amplification reaction such as PCR. Nucleic acid reagents used as synthesis intitation reagents (e.g., primers) in the reverse transcription and amplification steps of such an assay are preferably chosen from the p63 nucleic acid sequences described herein or are fragments thereof Preferably, the nucleic acid reagents are at least about 9 to 30 nucleotides in length. The amplification may be performed using, e.g., radioactively labeled or fluorescently labeled nucleotides, for detection. Alternatively, enough amplified product may be made such that the product can be visualized by standard ethidium bromide or other staining methods.

p63 gene expression assays of the invention may also be performed in situ (i.e., directly upon tissue sections of patient tissue, which may be fixed and/or frozen), thereby eliminating the need of nucleic acid purification. p63 nucleic acid reagents may be used as probes or as primers for such in situ procedures (see, for example, Nuovo, PCR In Situ Hybridization: Protocols And Application, 1992, Raven Press, New York). Alternatively, if a sufficient quantity of the appropriate cells can be obtained, standard Northern analysis can be performed to determine the level of p63 gene express by detecting levels of p63 mRNA.

EXAMPLES

The present invention may be better understood by reference to the following examples, which are provided by way of illustration and are not limiting.

Example 1

Immunohistochemical Study of Expression of p53-homolog p63 in Pulmonary Neoplasms p63 is a nuclear protein recently discovered in a screen for genes with homology to the tumor suppressor p53 gene. This Example describes p63 expression in benign lung tissue and neoplasms of pulmonary origin.

Materials and Methods

Tissues. Archival, routinely processed, formalin-fixed, paraffin-embedded surgical pathology specimens from bronchoscopic biopsy and pneumonectomy and/or lobectomy specimens were examined.

Antibody. The antibody used in this study was anti-p63 monoclonal antibody 4A4 (Santa Cruz Biotechnology, Inc., Santa Cruz Calif.). This antibody is reactive against a region common to both the full-length and truncated forms of p63.

Immunohistochemical staining. Five-micron-thick sections were heated and deparaffinized and were treated with 0.3% hydrogen peroxide to block endogenous peroxidase activity and pretreated with citric acid (pH 6.0) for antigen retrieval. Slides were then incubated overnight at room temperature with an anti-p63 antibody and stained using a streptavidin biotin-based immunoperoxidase staining kit (BioGenex, San Ramon, Calif.), according to the manufacturer's instructions. The kit employs diaminobenzidine as chromogen, and then counterstain with hematoxylin and/or eosin.

p63 expression was considered positive only if distinct nuclear staining was present. Intense positive staining of bronchial reserve cell nuclei was noted as an internal positive control for p63 staining of histologic sections.

Results

Normal epithelium. In normal lung, p63 intensely stained nuclei of bronchial reserve cells but did not stain ciliated cells, alveolar epithelial cells or non-epithelial cells. The lower strata of squamous metaplastic bronchial epithelium stained positively for p63.

Squamous cell carcinoma. Twenty-six out of twenty-seven cases (96%) of squamous cell carcinoma stained positively for p63. In well-differentiated carcinomas staining was generally inversely proportional to the degree of differentiation or keratinization as assessed by counterstaining slides with eosin. Staining, noted in basilar peristromal areas, diminished as cells became keratinized. In many keratinizing carcinomas, p63 expression was lost with onset of keratinization. However, in some cases, we noted keratinization with persisting p63 positivity, suggesting relative loss of cell regulatory suppression of proliferation concommitant with differentiation. Poorly differentiated carcinomas showed very high proportions (80–100%) of p63-positive nuclei.

Bronchioloalveolar carcinoma. Eight out of eight cases (100%) showed no detectable staining of tumor cell nuclei.

Adenocarcinoma. Staining of adenocarcinomas was variable: 9 out of 19 tumors showed no detectable staining. One out of 4 adenocarcinomas with alveolar spread showed positive staining.

Adenosquanous carcinomas. Two out of 3 adenosquamos carcinomas revealed a unique basalar staining pattern that approximated the pattern in normal ciliated bronchial epithelium.

Small cell undifferentiated carcinoma. Ten out often cases (100%) showed no detectable staining of tumor cell nuclei.

Carcinoid. Six out of six cases were almost entirely negative. Rare positive cells were of indeterminate, probably non-neoplastic origin and appeared morphologically distinct from the tumor cells.

Large cell carcinoma. Eight out of 12 tumors stained positively for p63.

Discussion p63 is a p53 homolog postulated to play a role in stem cell commitment in squamous epithelia. The activation of cell pathways that suppress cell division is essential for the commitment of undifferentiated dividing basalar cells to undergo maturation. Consistent with the known role of p53 as an activator of such suppressive pathways in cells responding to DNA damage, p63 might serve in a homologous physiologic role in normal stem cell commitment.

Accumulated data from several laboratories demonstrates expression of p63 in normal human cervical epidermis, hair follicles, and in stratified epidermal cultures, p63 protein is primarily restricted to cells with high proliferative potential and is absent from the cells that are undergoing terminal differentiation. In squamous cell carcinomas of the epidermis, the number of cells containing p63 and their distribution was found to depend on the degree of anaplasia. (Parsa et al, J. Invest. Dermatol. 1999, 113:1099–1105). In highly differentiated tumors, p63 was confined to a ring of basal-like cells surrounding, but at a distance from, centers of terminal differentiation. In less differentiated tumors, most cells contained p63 and their distribution was chaotic with respect to centers of terminal differentiation (Yamaguchi et al, Int. J. Cancer 2000, 86:684–9). FISH analysis shows amplification of the locus containing the p63 gene in primary head and neck carcinoma and in cervical carcinoma.

The results of the current study indicate that p53 homolog p63 stains poorly differentiated squamous cell carcinomas in a consistent and uniform manner with very high percentages (approaching 100%) of tumor cells showing nuclear staining. Staining in well differentiated squamous cell carcinomas is also observed to be strong but is apparent in basalar, para-stromal areas lacking keratinization. Staining of other lung tumor types revealed no staining in undifferentiated small-cell carcinomas and bronchioloalveolar carcinomas, and essentially negligible staining in carcinoids.

Adenocarcinomas showed varied staining patterns. When positive, the patterns differed from the staining pattern seen in squamous carcinomas.

One highly unusual pattern was that seen in two cases of adenosquamous carcinoma. The similarity of the unique basalar staining pattern to the staining of reserve cells in normal bronchial epithelium raises the possibility that this might be a form of adenocarcinoma in situ.

p63 expression appears to differ between bronchioloalveolar carcinoma and adenocarcinoma with alveolar spread: no cases of the former stained positively, whereas 1 out of 4 cases of the latter were p63-positive.

We have noted in other studies p63 staining in myoepithelial cells of breast; expression in thyroid follicular epithelial cells in Hashimoto's thyroiditis, and expression in a spectrum of other neoplasms. These include papillary thyroid carcinoma, urothelial carcinoma, endometrial adenocarcinoma and endocervical adenocarcinoma (see Examples 2 and 3, infra). Of potential significance, all of these tumors arising from non-squamous epithelia have the capacity to undergo squamous differentiation, and all are capable of expressing p63. In contrast, renal cell carcinomas, which never undergo squamous differentiation, do not express p63.

Ascertaining the specific tumor type in primary lung cancer has important implications, both for treatment and prognosis. Small cell undifferentiated carcinoma differs from the other histologic types in that it is a more aggressive tumor with a greater capacity for dissemination, therefore having a worse prognosis. For this reason, and because of greater chemosensitivity, the treatment of patients with small cell undifferentiated carcinoma is primarily chemotherapy. Surgery, on the other hand, is the therapy of choice for the remaining non-small cell lung carcinomas.

Distinction of poorly differentiated squamous carcinoma from small cell undifferentiated carcinoma can be difficult, particularly in small tumor samples found in cytopathologic specimens and in bronchoscopic biopsies. Previous studies have reported that the accuracy of diagnosis on bronchial brush specimens was 62 to 97.5% and specifically 53.8% for small cell undifferentiated carcinoma. Hence, using immunohistochemistry to determine the presence of p63 in cytologic specimens, which will distinguish a poorly-differentiated squamous cell carcinoma from a small cell undifferentiated carcinoma has evident clinical utility.

Example 2

Expression of p63 Protein in Subtypes of Transitional Cell and Renal Cell Carcinomas The p53 family of tumor suppressor genes includes p63, which is highly expressed in the basal layers of epithelial tissues. P63 may either promote apoptosis or antagonize p53, depending upon the expressed protein isoform. Expression of p63 has been found in transitional epithelium. Expression of p63 in transitional cell carcinomas was compared with expression in renal cell carcinomas. Non-cancerous tissues associated with the urinary tract were also examined.

Methods

Formalin-fixed, paraffin-embedded archival tissue from 81 patients was immunostained with p63 monoclonal antibody 4A4 (Santa Cruz) reactive against all subtypes of p63 protein as described above for Example 1. Immunostaining patterns and routine H&E staining patterns were interpreted by four observers. Nuclear staining was considered positive.

Results

Normal tissue. Benign adrenal cortex (1), prostate (2), and other benign kidney specimens were negative for p63 staining.

Transitional cell carcinomas. 96% of transitional cell carcinomas stained diffusely for p63, (low grade bladder 9/9, high grade bladder 10/22, ureter 2/2, renal pelvis 8/8). Bladder carcinoma-in-situ cases all stained (n=18) positively to varying degrees, including basal (about ½ of cases), diffuse, and rare. Cystitis cystica with focal dysplasia showed strong basal staining (1/1) for p63.

Renal cell carcinomas. In contrast all renal cell carcinoma specimens (21/21), regardless of type and grade, (including clear cell, papillary, chromophobe, and collecting duct) were negative as were xanthogranulomatous pyelonephritis (1).

Conclusion

Staining of p63 is strongly positive in transitional cell carcinomas and uniformly negative in renal cell carcinomas. This sharp distinction may be a useful diagnostic tool in preoperative evaluation and therapeutic planning in patients with upper urinary tract lesions.

Example 3

Expression of p63 in Papillary Thyroid Carcinoma and in Hashimoto's Thyroiditis

Nuclear proteins were discovered as a consequence of a screen for p53-homologous genes. Thus far, p63 expression has been demonstrated in basal cells of squamous epithelium and in urothelium. Immunohistochemical detection of p63 expression was evaluated in normal and abnormal thyroid tissue.

Materials and Methods

Five micron sections from routinely fixed and processed archival thyroid resection specimens were pretreated with citric acid pH 6.0 for antigen retrieval at 100° C. for 5 minutes, then incubated overnight with anti-p63 monoclonal antibody 4A4 (Santa Cruz). Slides were stained using a streptavidinbiotin kit (BioGenex), followed by reaction with diaminobenzidine, and then counterstaining with hematoxylin.

Results

Conditions negative for p63. No p63 expression was seen in normal thyroid tissue, twelve follicular adenomata, eleven Hurthle cell adenomata, six medullary carcinomas, two anaplastic carcinomas, and six Hurthle cell carcinomas. There was rare staining in one of seven follicular carcinomas. In addition, there was no p63 staining in ten nodular goiter samples, and one of 8 Grave's disease samples stained.

Hashimoto's thyroiditis. In contrast, seventy five percent (12/16) of Hashimoto's thyroiditis cases and seventy six percent (22/29) of papillary thyroid carcinomas showed epithelial cells with nuclear positivity for p63. Staining of tumor cells ranged from strong and/or frequent to weak and/or uncommon. In Hashimoto's cases, staining was characteristically intense but limited to several follicles. Of note, on parallel sections, CK19 positivity was found in p63-positive carcinomas but also in numerous benign follicles within areas of p63-positive thyroiditis.

Conclusions p63 is expressed in papillary thyroid carcinoma and in Hashimoto's thyroiditis. Considering the debated association of papillary thyroid carcinoma with Hashimoto's thyroiditis, it is possible that p63 may be a potential pathobiologic link between the two disorders.

p63 may also be of use in distinguishing papillary carcinoma from other thyroid neoplasms, particularly on fine needle aspirates. This observation has particular relevance for avoiding unnecessary surgery because of a misdiagnosis or the inability to diagnose nodular goiter instead of papillary carcinoma.

Example 4

Detecting p63 in Non-Traumatically Obtained Samples

In this example, we describe results of examination of pre-cancerous squamous intra-epithelial lesions of the uterine cervix compared with normal cervical epithelium.

Methods

Cervical and vaginal epithelial cells were obtained from gentle swabbing of the uppermost layers and subjected to immunostaining for p63 as described infra.

Results

In contrast to normal epithelium, in which p63 is expressed in the lower cell layers of the epithelium, in accordance with findings by others, p63 expression is found in the uppermost layers of high grade squamous intraepithelial lesions.

Discussion

Since the papanicolaou "pap" smear of the cervical and vaginal epithelium involves sampling of the uppermost cell layers of these epithelia via gentle, non-traumatic swabbing, brushing or other non-traumatic sampling means, detection of p63 alone, or in a multiplex panel with other markers, in cells from cervix or vaginal squamous epithelium can be used to signify the presence of a clinically advanced squamous intraepithelial lesion. This can be adapted for automated screening for aberrant expression of p63 in cells from the uppermost layers of cervical-vaginal squamous epithelium in cervical-vaginal smears, as a substitute for manual screening presently performed on millions of pap smears to detect such lesions.

Similarly, detection of cancer or pre-cancerous changes by detecting p63 (at the gene, mRNA, or protein level) in a cell or fluid sample following non-traumatic sampling (such as lavage, gentle brush, wash) of other epithelia in which abnormal p63-positive epithelia replace normal epithelia (the uppermost layer of cells of which are normally p63-negative) constitutes another claim of this patent. This applies not only to cervical vaginal sampling, but to sampling of oral, upper respiratory tract, lower respiratory tract, esophageal, cyst content samples or cyst lining, urinary tract, endocervical, endometrial, and other surfaces or mucosae.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

It is further to be understood that all values are approximate, and are provided for description.

Patents, patent applications, publications, product descriptions, and protocols are cited throughout this application, the disclosures of which are incorporated herein by reference in their entireties for all purposes.

What is claimed is:

1. A method for distinguishing a differentiated squamous cell lung cancer carcinoma from an undifferentiated lung cancer carcinoma, which method comprises detecting p63 expression in cells from a lung carcinoma, wherein consistent p63 expression indicates that the lung carcinoma is a squamous cell lung carcinoma and the absence of p63 expression indicates that the lung carcinoma is an undifferentiated lung carcinoma.

2. The method according to claim 1 wherein detecting p63 expression comprises detecting expression of p63 protein.

3. The method according to claim 2 wherein detecting p63 protein expression comprises detecting the p63 protein with an immunoassay.

4. The method according to claim 3 wherein the immunoassay is an immunohistochemical assay.

5. The method according to claim 1 wherein the differentiated lung carcinoma is selected from the group consisting of a poorly differentiated squamous cell carcinoma, a moderately differentiated squamous cell carcinoma, and a well differentiated squamous cell carcinoma.

6. The method according to claim 1 wherein the differentiated lung carcinoma is a poorly differentiated squamous cell carcinoma.

7. The method according to claim 1 wherein the undifferentiated lung carcinoma is a small cell undifferentiated carcinoma.

* * * * *

UNITED STATES PATENT AND TRADEMARK OFFICE
CERTIFICATE OF CORRECTION

| | |
|---|---|
| PATENT NO. | : 6,972,181 B2 |
| APPLICATION NO. | : 10/043502 |
| DATED | : December 6, 2005 |
| INVENTOR(S) | : David E. Burstein |

It is certified that error appears in the above-identified patent and that said Letters Patent is hereby corrected as shown below:

Column 1, Lines 7-10, delete "The research leading to the present invention was supported, in part, by the National Cancer Institute Grant No. R21-CA81362. Accordingly, the U.S. Government may have certain rights in the invention." and substitute therefore --This invention was made with government support under grant R21-CA81362 awarded by the National Cancer Institute. The government has certain rights in the invention.--

Signed and Sealed this
Fifth Day of June, 2012

David J. Kappos
*Director of the United States Patent and Trademark Office*